(12) United States Patent
Fan et al.

(10) Patent No.: US 12,178,660 B2
(45) Date of Patent: Dec. 31, 2024

(54) ECHOGENICITY QUANTITATIVE TEST SYSTEM FOR AN ECHOGENIC MEDICAL DEVICE

(71) Applicant: BECTON, DICKINSON AND COMPANY, Franklin Lakes, NJ (US)

(72) Inventors: Qingqing Fan, Shanghai (CN); Irene Gao, Shanghai (CN)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 1107 days.

(21) Appl. No.: 17/000,540

(22) Filed: Aug. 24, 2020

(65) Prior Publication Data

US 2021/0055414 A1 Feb. 25, 2021

(30) Foreign Application Priority Data

Aug. 22, 2019 (CN) .......................... 201921364733.8

(51) Int. Cl.
| A61B 8/00 | (2006.01) |
| G01S 15/89 | (2006.01) |
| G06T 7/00 | (2017.01) |
| G06V 10/22 | (2022.01) |
| G06V 10/98 | (2022.01) |

(52) U.S. Cl.
CPC ............ *A61B 8/58* (2013.01); *G01S 15/8938* (2013.01); *G06T 7/0012* (2013.01); *G06V 10/22* (2022.01); *G06V 10/993* (2022.01); *G06T 2207/10132* (2013.01); *G06T 2207/30004* (2013.01)

(58) Field of Classification Search
CPC .................................................. G01S 15/8938
See application file for complete search history.

(56) References Cited

U.S. PATENT DOCUMENTS

| 6,171,248 | B1 | 1/2001 | Hossack et al. |
| 6,190,915 | B1 | 2/2001 | Madsen et al. |
| 6,238,343 | B1 | 5/2001 | Madsen et al. |
| 6,368,277 | B1 | 4/2002 | Mao |
| 6,494,860 | B2 | 8/2002 | Rocamora |
| 6,520,934 | B1 | 2/2003 | Lee et al. |
| 6,540,721 | B1 | 4/2003 | Voyles |
| 6,589,262 | B1 | 7/2003 | Honebrink |
| 6,599,237 | B1 | 7/2003 | Singh |
| 6,605,943 | B1 | 8/2003 | Clark |

(Continued)

*Primary Examiner* — Walter L Lindsay, Jr.
*Assistant Examiner* — Andrew V Do
(74) *Attorney, Agent, or Firm* — Dickinson Wright PLLC; Andrew D. Dorisio

(57) ABSTRACT

An echogenicity quantitative test system for a sample echogenic medical device includes a fixture into which the echogenic medical device is positioned in relation to an ultrasonic probe connected with an ultrasound diagnostic device. The fixture includes a frame; a probe holder having a first guide rod and a probe clamp configured to hold the ultrasonic probe and movably held on the first guide rod, and a sample holder having a second guide rod and a sample clamp configured to hold the medical device sample. The sample clamp is movably held on the second guide rod. The frame may include guide rails, and the first guide rod and the second guide rod are movably disposed in the guide rails so as to allow for adjustments to the relative positions of the ultrasonic probe and the sample echogenic medical device.

15 Claims, 3 Drawing Sheets

(56) References Cited

U.S. PATENT DOCUMENTS

| | | |
|---|---|---|
| 6,647,132 B1 | 11/2003 | Montillo |
| 6,663,595 B2 | 12/2003 | Spohn |
| 6,673,060 B1 | 1/2004 | Fleming, III |
| 6,692,464 B2 | 2/2004 | Graf |
| 6,723,052 B2 | 4/2004 | Mills |
| 6,733,489 B2 | 4/2004 | Nutting |
| 6,736,803 B2 | 5/2004 | Cawood |
| 6,796,991 B2 | 5/2004 | Nardeo |
| 6,748,973 B2 | 6/2004 | Lindroos |
| 6,892,087 B2 | 5/2005 | Osypka |
| 6,905,458 B2 | 6/2005 | Choay et al. |
| 6,939,370 B2 | 9/2005 | Hartley |
| 7,001,369 B2 | 2/2006 | Griffin et al. |
| 7,001,396 B2 | 2/2006 | Glazier et al. |
| 7,048,717 B1 | 5/2006 | Frassica |
| 7,101,353 B2 | 9/2006 | Lui et al. |
| 7,104,979 B2 | 9/2006 | Jansen et al. |
| 7,153,277 B2 | 12/2006 | Skujins et al. |
| 7,158,692 B2 | 1/2007 | Chalana et al. |
| 7,217,256 B2 | 5/2007 | Di Palma |
| 7,258,669 B2 | 8/2007 | Russell |
| 7,276,062 B2 | 10/2007 | McDaniel et al. |
| 7,306,585 B2 | 12/2007 | Ross |
| 7,314,481 B2 | 1/2008 | Karpiel |
| 7,322,959 B2 | 1/2008 | Warnack et al. |
| 7,462,488 B2 | 12/2008 | Madsen et al. |
| 7,481,805 B2 | 1/2009 | Magnusson |
| 7,510,568 B2 | 3/2009 | Bleam et al. |
| 7,524,305 B2 | 4/2009 | Moyer |
| 7,534,250 B2 | 5/2009 | Schaeffer et al. |
| 7,578,814 B2 | 8/2009 | Accisano, III et al. |
| 7,591,813 B2 | 9/2009 | Levine et al. |
| 7,655,021 B2 | 2/2010 | Brasington et al. |
| 7,677,078 B2 | 3/2010 | Sauer et al. |
| 7,678,100 B2 | 3/2010 | Chin et al. |
| 7,704,245 B2 | 4/2010 | Dittman et al. |
| 7,722,567 B2 | 5/2010 | Tal |
| 7,736,331 B2 | 6/2010 | Accisano, III et al. |
| 7,780,715 B2 | 8/2010 | Shaked et al. |
| 7,794,402 B2 | 9/2010 | Wang |
| 7,833,597 B2 | 11/2010 | Bavaro et al. |
| 7,857,820 B2 | 12/2010 | Skakoon et al. |
| 7,874,987 B2 | 1/2011 | Altmann et al. |
| 7,875,021 B2 | 1/2011 | Minassians |
| 7,879,024 B2 | 2/2011 | Thorstenson et al. |
| 7,909,798 B2 | 3/2011 | Osypka |
| 7,909,814 B2 | 3/2011 | Accisano, III et al. |
| 7,922,696 B2 | 4/2011 | Tal et al. |
| 7,951,093 B2 | 5/2011 | Skujins et al. |
| 7,961,929 B2 | 6/2011 | Ni et al. |
| 7,968,038 B2 | 6/2011 | Dittman et al. |
| 7,985,232 B2 | 7/2011 | Potter et al. |
| 7,993,272 B2 | 8/2011 | Chomas et al. |
| 7,993,305 B2 | 8/2011 | Ye et al. |
| 8,070,694 B2 | 12/2011 | Galdonik et al. |
| 8,105,287 B2 | 1/2012 | Fisher et al. |
| 8,137,309 B2 | 3/2012 | Nishtala et al. |
| 8,137,317 B2 | 3/2012 | Osypka |
| 8,147,452 B2 | 4/2012 | Nardeo et al. |
| 8,147,456 B2 | 4/2012 | Fisher et al. |
| 8,157,790 B2 | 4/2012 | Kubo et al. |
| 8,177,770 B2 | 5/2012 | Rasmussen et al. |
| 8,262,671 B2 | 9/2012 | Osypka |
| 8,273,059 B2 | 9/2012 | Nardeo et al. |
| 8,287,585 B2 | 10/2012 | Gurm |
| 8,292,852 B2 | 10/2012 | Mulholland et al. |
| 8,366,674 B2 | 2/2013 | Frassica et al. |
| 8,377,083 B2 | 2/2013 | Mauch et al. |
| 8,460,323 B2 | 6/2013 | Mauch et al. |
| 8,478,383 B2 | 7/2013 | Bar-Tal et al. |
| 8,500,688 B2 | 8/2013 | Engel et al. |
| 8,517,993 B2 | 8/2013 | Freas et al. |
| 8,591,567 B2 | 11/2013 | Chau et al. |
| 8,639,310 B2 | 1/2014 | Chen et al. |
| 8,652,098 B2 | 2/2014 | Haslinger |
| 8,696,582 B2 | 4/2014 | Rohling |
| 8,700,129 B2 | 4/2014 | Hauck et al. |
| 8,734,426 B2 | 5/2014 | Ahmed et al. |
| 8,753,313 B2 | 6/2014 | Kimmel et al. |
| 8,771,225 B2 | 7/2014 | Ahn |
| 8,795,311 B2 | 8/2014 | Griffith et al. |
| 8,827,958 B2 | 9/2014 | Bierman et al. |
| 8,834,499 B2 | 9/2014 | Mauch et al. |
| 8,845,614 B2 | 9/2014 | Raabe et al. |
| 8,888,787 B2 | 11/2014 | Wynberg |
| 8,906,268 B2 | 12/2014 | Boutet et al. |
| 8,911,400 B2 | 12/2014 | Ferry |
| 8,926,560 B2 | 1/2015 | Dinh et al. |
| 8,948,474 B2 | 2/2015 | Chang et al. |
| 8,986,283 B2 | 3/2015 | Rajendran et al. |
| 8,998,814 B2 | 4/2015 | Oikawa et al. |
| 9,044,266 B2 | 6/2015 | Nimgaard |
| 9,044,577 B2 | 6/2015 | Bishop et al. |
| 9,060,756 B2 | 6/2015 | Bencini et al. |
| 9,089,672 B2 | 7/2015 | Hendriksen et al. |
| 9,126,019 B2 | 9/2015 | Guo et al. |
| 9,149,176 B2 | 10/2015 | Greenberg et al. |
| 9,149,606 B2 | 10/2015 | Beissel et al. |
| 9,174,036 B2 | 11/2015 | Okamura et al. |
| 9,186,484 B2 | 11/2015 | Defossez et al. |
| 9,233,226 B2 | 1/2016 | Lampropoulos et al. |
| 9,241,735 B2 | 1/2016 | Nishtala et al. |
| 9,242,076 B2 | 1/2016 | Burton et al. |
| 9,248,261 B2 | 2/2016 | Schweikert et al. |
| 9,254,146 B2 | 2/2016 | Massengale et al. |
| 9,282,945 B2 | 3/2016 | Smith et al. |
| 9,314,749 B2 | 4/2016 | Yagi et al. |
| 9,352,132 B2 | 5/2016 | Urie |
| 9,393,041 B2 | 7/2016 | Barker et al. |
| 9,398,936 B2 | 7/2016 | Razzaque et al. |
| 9,409,001 B2 | 8/2016 | Aggerholm et al. |
| 9,420,992 B2 | 8/2016 | Sheldon et al. |
| 9,445,837 B2 | 9/2016 | Fulton, III |
| 9,474,882 B2 | 10/2016 | Franklin |
| 9,492,638 B2 | 11/2016 | McKinnis et al. |
| 9,498,282 B2 | 11/2016 | Fernald |
| 9,504,476 B2 | 11/2016 | Gulachenski |
| 9,517,185 B1 | 12/2016 | Al-Jazaeri |
| 9,522,253 B2 | 12/2016 | Gandras et al. |
| 9,538,981 B2 | 1/2017 | Rioux et al. |
| 9,539,415 B2 | 1/2017 | Racz et al. |
| 9,545,506 B2 | 1/2017 | Quigley |
| 9,566,087 B2 | 2/2017 | Bierman et al. |
| 9,566,413 B2 | 2/2017 | Eberhardt et al. |
| 9,629,981 B2 | 4/2017 | Thungana et al. |
| 9,655,594 B2 | 5/2017 | Oraevsky et al. |
| 9,668,654 B2 | 6/2017 | Rajendran et al. |
| 9,693,820 B2 | 7/2017 | Potter et al. |
| 9,706,988 B2 | 7/2017 | Nobles et al. |
| 9,717,884 B2 | 8/2017 | Matsumoto et al. |
| 9,737,284 B2 | 8/2017 | Kim et al. |
| 9,764,111 B2 | 9/2017 | Gulachenski |
| 9,764,117 B2 | 9/2017 | Bierman et al. |
| 9,773,307 B2 | 9/2017 | Chang et al. |
| 9,839,770 B2 | 12/2017 | Linden et al. |
| 9,861,385 B2 | 1/2018 | Fulton |
| 9,872,666 B2 | 1/2018 | Quearry |
| 9,877,704 B2 | 1/2018 | Ogawa |
| 9,884,169 B2 | 2/2018 | Bierman et al. |
| 9,920,188 B2 | 3/2018 | Vogt et al. |
| 9,950,158 B2 | 4/2018 | True et al. |
| 9,955,940 B1 | 5/2018 | Coats et al. |
| 9,972,082 B2 | 5/2018 | Holsing et al. |
| 9,980,699 B2 | 5/2018 | Quearry et al. |
| 10,004,475 B2 | 6/2018 | Quearry |
| 10,010,701 B2 | 7/2018 | Ahmed et al. |
| 10,034,655 B2 | 7/2018 | McKinnis et al. |
| 10,074,037 B2 | 9/2018 | Lu et al. |
| 10,076,307 B2 | 9/2018 | Coats et al. |
| 10,080,873 B2 | 9/2018 | Stapleton et al. |
| 10,086,174 B2 | 10/2018 | Crall et al. |
| 10,111,645 B2 | 10/2018 | Fearnot et al. |
| 10,118,027 B2 | 11/2018 | Seifert et al. |
| 10,137,020 B2 | 11/2018 | Treacy et al. |

(56) References Cited

U.S. PATENT DOCUMENTS

| | | |
|---|---|---|
| 10,143,455 B2 | 12/2018 | Lichty, II et al. |
| 10,166,070 B2 | 1/2019 | Davies et al. |
| 10,169,641 B2 | 1/2019 | Lee et al. |
| 10,173,033 B2 | 1/2019 | Leung et al. |
| 10,182,804 B2 | 1/2019 | Walters et al. |
| 10,183,147 B2 | 1/2019 | Yang et al. |
| 10,188,371 B2 | 1/2019 | Madsen et al. |
| 10,213,582 B2 | 2/2019 | Garrison et al. |
| 10,213,583 B2 | 2/2019 | Klocke et al. |
| 10,219,788 B2 | 3/2019 | Tabeie |
| 10,220,192 B2 | 3/2019 | Drasler et al. |
| 10,226,203 B2 | 3/2019 | Stigall et al. |
| 10,226,264 B2 | 3/2019 | McIntosh et al. |
| 10,238,463 B2 | 3/2019 | Verstege et al. |
| 10,238,834 B2 | 3/2019 | Bridgeman et al. |
| 10,249,037 B2 | 4/2019 | Chang et al. |
| 10,252,028 B2 | 4/2019 | Katsurada et al. |
| 2008/0132933 A1 | 6/2008 | Gerber |
| 2009/0030370 A1 | 1/2009 | Nishtala et al. |
| 2011/0128552 A1* | 6/2011 | Hadcock .............. G01B 11/105 356/496 |
| 2011/0181614 A1 | 7/2011 | Chang et al. |
| 2011/0224538 A1 | 9/2011 | Linares |
| 2013/0103004 A1 | 4/2013 | Gray et al. |
| 2013/0190609 A1 | 7/2013 | Fischer, Jr. |
| 2013/0226094 A1 | 8/2013 | Ahmed et al. |
| 2014/0180068 A1 | 6/2014 | Spencer et al. |
| 2014/0206987 A1 | 7/2014 | Urbanski et al. |
| 2014/0221828 A1 | 8/2014 | Mckinnis et al. |
| 2014/0257090 A1 | 9/2014 | Fischer, Jr. et al. |
| 2014/0265024 A1 | 9/2014 | Quearry |
| 2014/0276073 A1 | 9/2014 | Quearry |
| 2015/0086094 A1 | 3/2015 | Chang et al. |
| 2015/0086095 A1 | 3/2015 | Chang et al. |
| 2015/0112256 A1 | 4/2015 | Byrne et al. |
| 2015/0150586 A1 | 6/2015 | Aggerholm et al. |
| 2015/0272542 A1 | 10/2015 | Shuman et al. |
| 2015/0273120 A1 | 10/2015 | Zamarripa et al. |
| 2015/0320979 A1 | 11/2015 | Fearnot et al. |
| 2016/0120509 A1 | 5/2016 | Syed et al. |
| 2016/0128718 A1 | 5/2016 | Aggerholm et al. |
| 2016/0193448 A1 | 7/2016 | Nardeo et al. |
| 2016/0223308 A1 | 8/2016 | Rhee et al. |
| 2016/0331929 A1 | 11/2016 | Lampropoulos et al. |
| 2017/0021139 A1 | 1/2017 | Bajema et al. |
| 2017/0032557 A1 | 2/2017 | Anand et al. |
| 2017/0049997 A1 | 2/2017 | Chao et al. |
| 2017/0112528 A1 | 4/2017 | Crisman et al. |
| 2017/0135908 A1 | 5/2017 | Tai et al. |
| 2017/0143349 A1 | 5/2017 | Raabe et al. |
| 2017/0151415 A1 | 6/2017 | Maeda et al. |
| 2017/0173302 A1 | 6/2017 | Beasley et al. |
| 2017/0182297 A1 | 6/2017 | Lysgaard et al. |
| 2017/0182304 A1 | 6/2017 | Bagwell et al. |
| 2017/0189059 A1 | 7/2017 | Long, Jr. et al. |
| 2017/0224967 A1 | 8/2017 | Gorn et al. |
| 2017/0232231 A1 | 8/2017 | Neoh et al. |
| 2017/0252560 A1 | 9/2017 | Imran |
| 2017/0296798 A1 | 10/2017 | Kume et al. |
| 2017/0333149 A1 | 11/2017 | Stigall et al. |
| 2017/0333682 A1 | 11/2017 | Nardeo |
| 2017/0368238 A1 | 12/2017 | Robinson |
| 2018/0001063 A1 | 1/2018 | Aggerholm et al. |
| 2018/0008237 A1 | 1/2018 | Venkataraman et al. |
| 2018/0015277 A1 | 1/2018 | Stephens et al. |
| 2018/0036033 A1 | 2/2018 | Ignagni et al. |
| 2018/0093073 A1 | 4/2018 | Shimizu et al. |
| 2018/0117279 A1 | 5/2018 | Yachia et al. |
| 2018/0126129 A1 | 5/2018 | McDonough |
| 2018/0132821 A1 | 5/2018 | Dehghan Marvast et al. |
| 2018/0169383 A1 | 6/2018 | Khalaj et al. |
| 2018/0177980 A1 | 6/2018 | Khalaj et al. |
| 2018/0214288 A1 | 8/2018 | Smouse et al. |
| 2018/0221649 A1 | 8/2018 | Mulrooney et al. |
| 2018/0243046 A1 | 8/2018 | Scott et al. |
| 2018/0256849 A1 | 9/2018 | Linden et al. |
| 2018/0256907 A1 | 9/2018 | Katra et al. |
| 2018/0263595 A1 | 9/2018 | Goksel et al. |
| 2018/0272039 A1 | 9/2018 | Kim et al. |
| 2018/0296186 A1 | 10/2018 | Harks et al. |
| 2018/0296804 A1 | 10/2018 | Bierman |
| 2018/0360494 A1 | 12/2018 | Melsheimer |
| 2019/0001031 A1 | 1/2019 | Real et al. |
| 2019/0015638 A1 | 1/2019 | Gruba et al. |
| 2019/0053790 A1 | 2/2019 | Grover et al. |
| 2019/0059857 A1 | 2/2019 | Ogura et al. |
| 2019/0076166 A1 | 3/2019 | Bierman et al. |
| 2019/0076167 A1 | 3/2019 | Fantuzzi et al. |
| 2019/0083061 A1 | 3/2019 | Choi |
| 2019/0091453 A1 | 3/2019 | Browne et al. |
| 2019/0091461 A1 | 3/2019 | Bonham et al. |
| 2019/0105466 A1 | 4/2019 | Schibli et al. |
| 2019/0105474 A1 | 4/2019 | Sheibley |
| 2019/0110795 A1 | 4/2019 | Koo et al. |
| 2019/0125318 A1 | 5/2019 | Sarna et al. |
| 2019/0125398 A1 | 5/2019 | Baldwin et al. |

* cited by examiner

ECHOGENICITY QUANTITATIVE TEST SYSTEM FOR AN ECHOGENIC MEDICAL DEVICE

This application claims the benefit of Chinese Utility Model No. 201921364733.8, filed Aug. 22, 2019, the disclosure of which is incorporated herein by reference.

TECHNICAL FIELD

The present disclosure relates to an echogenicity quantitative test system for an echogenic medical device.

BACKGROUND

Ultrasonography has become more and more popular in clinical applications, and under many circumstances is the first option in gynecological, celiac and cardiac diagnosis, because it is atraumatic, fast and cheap.

With the development of interventional ultrasonography, B mode grayscale ultrasonic images are increasingly used under the assistance of echogenic medical devices to monitor the puncture on-line so as to reduce the failure rate of the extra trauma risk. However, one issue for medical device manufacturers is how to characterize the echogenicity quantitatively during the product developing period.

Although researchers realized that quantification of echogenicity was critical to a standard echo analysis over the past decades, the clinical judgment on echogenicity mainly relies on subjective evaluation to describe the morphology and brightness of region of interest (ROI). So far, there have not been standard or guidance on suggesting a quantitative method for echogenicity analysis.

There have been some attempts to give quantitative description on B mode grayscale images commonly applied on carotid plaques/stenosis, efforts focused on tissue classification has been quite limited. In these attempts, all data (to be specific, B mode images) were produced by experienced sonographer with at least ten years of clinical ultrasonic diagnosis experience, who were focused on looking for the relation between quantitative analysis results and historical results for plaque or certain tissues. Few have paid attention to quantitative analysis of medical devices to guide the characterization of echogenic devices.

Some previous works on ultrasound assessment of liver or kidney of infants somehow provided a basis for further studies by establishing an index for ultrasonic brightness of gray-level histogram with the tests on a standard tissue-mimicking material (A. C. Lamont, "Ultrasound assessment of liver and kidney brightness in infants, use of the gray-level histogram," Investigative Radiology, 1995, 30(4), 232-238, the disclosure of which is incorporated herein by reference). However, little further work results were searched. Quantitative analysis on gray-level images was mainly applied in the carotid plaques. One work assessed echogenicity by integrated backscatter analysis on plaques, but required to make measurement only with certain ultrasonic devices (K. Nagano et al, "Quantitative evaluation of carotid plaque echogenicity by integrated backscatter analysis: correlation with symptomatic history and histologic findings," Cerebrovascular Diseases, 2008, 26, 578-583, the disclosure of which is incorporated herein by reference).

Other works made efforts on pixel analysis for gray-level images with in-house written program or common commercial picture processing software, among which Adobe Photoshop is a widely applied one. One work even discussed the comparison between two different image-analysis software.

With all the efforts, researchers worked to find the correlations between gray-scale median (GSM) to historical analysis on tissue textures. It is actually very difficult to identify a standard method on analysis images from different Ultrasonic equipment with various parameter settings, because the absolute value for ROI brightness is affected by the equipment itself, probe type and gains setting. A further development on GSM calculation was a normalization method by defining GSM of blood as 0 and GSM of adventitia as another data in advance. Some efforts went to good results with certain correlations, while some efforts did not.

Others have realized the different dispersion of brightness of plaque with the same GSM value, indicated that GSM in the region of interest reflects, to some extent, absolute brightness of only a small partial, but can hardly reflect the average brightness of ROI (D. Craiem et al, "Atheromatous plaques: quantitative analysis of the echogenicity of different layers," Rev Esp Cardiol, 2009, 62(9) 984-991, the disclosure of which is incorporated herein by reference).

Still others have applied the GSM method to classify the dataset on other tissues of blood, lipid, muscle, fiber and calcium (D. V. Pazinota, "Pixel-level tissue classification for ultrasound images," IEEE Journal of Biomedical and Health Informatics, 2016, 20(1), 256-267, the disclosure of which is incorporated herein by reference). This involved using the previous definition of GSM for defining blood and adventitia as 0 and 190, respectively. The correlation between GSM analysis and historical results in their work was relatively low.

Yet others performed quantitative analysis on kidney by using the liver as a reference (J. A. Manley, "How echogenic is echogenic? Quantitative acoustics of the renal cortex," American Journal of Kidney Diseases, 2001, 37(4), 706-711, the disclosure of which is incorporated by reference). However, this did not involve making the normalization by defining a certain ROI as maximum and minimum pixel density. Similar work was performed in which quantitative characterization on renal tissue with GSM method was used by defining fully black area as 0 and renal fascia as 200, and further suggested a gray range for different renal tissues (A. Luiza, "Ultrasound tissue characterization of the normal kidney," Ultrasound Quarterly, 2012, 28(4)275-280, the disclosure of which is incorporated herein by reference).

Accordingly, a need is identified for a standard test system for quantitative characterization of echogenicity for medical devices used for on-line monitoring during surgery, such as by identifying the brightness difference in mean value of ROI to environment in gray-level ultrasonic images.

SUMMARY

The present disclosure is aimed at providing a standard test system for quantitative characterization of echogenicity for medical devices used for on-line monitoring during surgery, by identifying the brightness difference in a mean value of a region of interest (ROI) to the environment in gray-level ultrasonic images. For example, the present disclosure may be used for performing an echogenic test for medical devices for percutaneous nephrolithotomy, or PCNL, surgery. For example, the echogenic medical device may be a balloon dilator (or balloon catheter). The present disclosure can also be used to test the echogenicity of a test medium.

According to the present disclosure, an echogenicity quantitative test system for echogenic medical devices is provided. The system comprises a test fixture and an ultrasound diagnostic device. The test fixture comprises a frame, a probe holder having a first guide rod and a probe clamp configured to hold an ultrasonic probe and movably held on the first guide rod. The ultrasonic probe may be connected to the ultrasound diagnostic device.

A sample holder includes a second guide rod and a device sample clamp configured to hold the medical device sample. The sample clamp is movably held on the second guide rod. The first and second guide rods may be provided on the frame, and each of the first guide rod and the second guide rod are movably disposed on guide rails.

According to one embodiment, with the probe clamp immovably fixed on the first guide rod, the medical device sample clamp is movable along the second guide rod. The medical device sample clamp may be immovably fixed on the second guide rod, and the probe clamp is movable along the first guide rod. The probe clamp may be movable along the first guide rod, while the sample clamp is movable along the second guide rod. The second guide rod may be perpendicular to an ultrasonic array acoustic wave emitting plane of the ultrasonic probe. The sample clamp may be rotatable about the second guide rod so as to allow an angle adjustment.

According to another aspect the echogenicity quantitative test system for echogenic medical devices further comprises a container configured to hold a test medium and a lifting platform located directly below the ultrasonic probe. The container may be placed onto the lifting platform. The frame may be a closed frame or an open frame.

The ultrasonic probe may have a main plane and a thickness. An ultrasonic array acoustic wave emitting plane of the ultrasonic probe may be parallel to the main plane and perpendicular to the thickness. The main plane of the probe may be perpendicular to the first guide rod and the second guide rod.

The ultrasonic diagnostic device may comprise an analysis unit configured to read a mean grayscale value of a region of interest of the echogenic medical device sample or the test medium, read a mean grayscale value of an adjacent region having a similar number of pixels as the region of interest, and calculate a difference between the mean grayscale value of the region of interest and the mean grayscale value of the adjacent region. The analysis unit may be configured to calculate at least three differences between the mean grayscale value of the region of interest and the mean grayscale value of the adjacent region, and calculate a mean value of the at least three differences.

BRIEF DESCRIPTION OF THE DRAWINGS

Other features of the present disclosure will become apparent from the following description of exemplary embodiments with reference to the drawings.

DETAILED DESCRIPTION

Embodiments of the present disclosure will hereinafter be described with reference to the accompanying drawings. Examples of echogenic medical devices include medical devices for PCNL surgery. For example, the echogenic medical device may be a balloon dilator (or balloon catheter). However, it should be noted that examples of echogenic medical devices are not limited thereto. Depending on specific applications, the echogenic medical devices may be other medical devices known to those skilled in the art, such as abdominal medical devices, gynecological and obstetric medical devices, cardiac medical devices, and so on.

Embodiments described below serve only as specific examples. However, the present disclosure is not limited to the embodiments described in the description.

The quantitative test system for echogenicity of echogenic medical devices mainly includes the following aspects: a test fixture 10 for clamping the ultrasonic probe and the medical device sample; an ultrasound diagnostic device 20; a test medium 21; and a pixel analysis method.

Test Fixture for Clamping the Ultrasonic Probe and the Sample Medical Device

Figure 1:
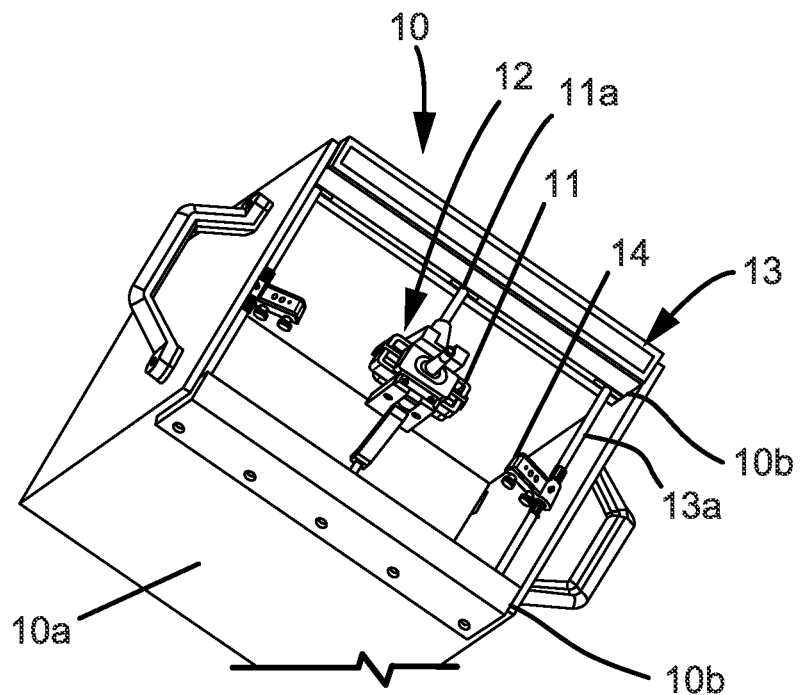
FIG. 1 is a top perspective view of an echogenicity quantitative test system according to the present disclosure.

The test fixture 10 is provided to minimize the unexpected variations caused by improper holding of the medical device sample and ultrasound probe during testing. As shown in FIG. 1, the fixture 10 comprises a frame 10a. According to an embodiment, the frame 10a may have a cuboid shape.

The fixture 10 may further comprise a probe holder 11 having a first guide rod 11a and a probe clamp 12 (shown in an enlarged view in FIG. 2) configured to hold an ultrasonic probe 16, the probe clamp 12 being movably held on the first guide rod 11a. A sample holder 13 includes a second guide rod 13a and a sample clamp 14 configured to clamp a medical device sample 17 (see FIGS. 3 and 6), the medical device sample clamp 14 being movably held on the second guide rod. Opposed guide rails 10b are provided on the frame 10a, and both ends of each of the first guide rod 11a and the second guide rod 13a are movably disposed in the guide rails.

Figure 2:
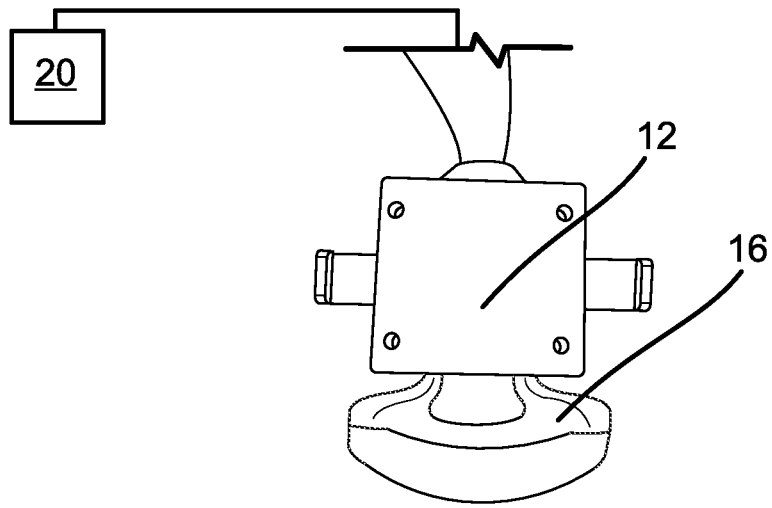
FIG. 2 is a top view of a probe clamp in an echogenicity quantitative test system according to the present disclosure.

As shown in FIG. 2, a shape of the probe clamp 12 can be adjusted according to a profile of the ultrasonic probe 16 so as to ensure that the probe holder 11 can stably hold the ultrasonic probe 16.

By translating the first guide rod 11a and the second guide rod 13a in the guide rails 10b of the frame 10a, a relative position or distance between the probe clamp 12 and the sample clamp 14 can be adjusted. Consequently, a relative position or distance between the medical device sample 17 and the ultrasound probe 16 can be adjusted.

Further, a distance between the probe holder 11 and the sample holder 13 may need adjustment to better simulate the actual application. One approach is to fix the probe clamp 12 and adjust the position of the medical device sample 17 by moving the sample clamp 14 on the second guide rod 13a in a direction D1 (such as perpendicular to the ultrasonic array of the probe 16 that emits acoustic waves, and details will be described later). Other approaches could involve fixing the medical device sample clamp 14 and moving the probe clamp 12 along the first guide rod 11a, or moving simultaneously the probe clamp 12 along the first guide rod 11a and moving the sample clamp 14 along the second guide rod 13a.

Figure 3:
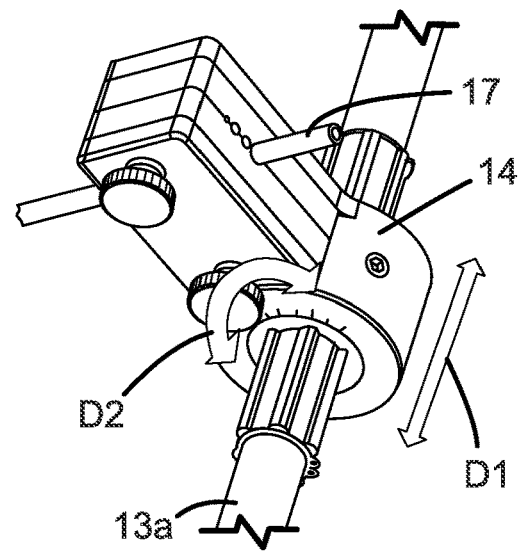
FIG. 3 is a perspective view of a medical device sample holder of an echogenicity quantitative test system according to the present disclosure.

The sample clamp 14 may also be rotatably adjustable such that the medical device sample 17 is rotatably adjustable. In particular, as shown in FIG. 3, in addition to being translatable along the second guide rod 13a, the sample clamp 14 is also rotatable around the second guide rod 13a in a direction D2 perpendicular to the direction D1 so as to allow adjustment of a test angle. For example, in the case where the medical device sample is a balloon dilator, a puncture angle of the balloon dilator in actual application can be better simulated by rotating the sample clamp 14.

Test Medium and Fixture Set-Up

The quantitative test system for echogenicity further comprises a container 15 configured to hold a test medium. Various test media can be used to fill the container 15. Test medium 21 should be stable from the statistical point of view, and close to clinical application environment. Simulated fluids, biological tissues, or cadaver organs are suitable options.

Figure 4:
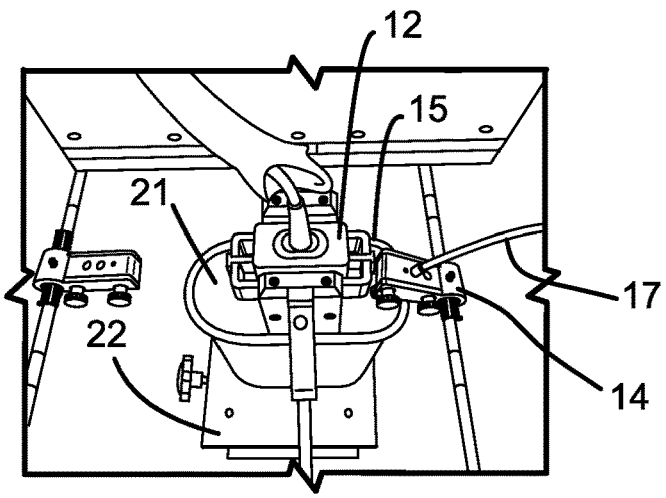
FIG. 4 is a top perspective view of an echogenicity quantitative test system according to the present disclosure.

As shown in FIG. 4, the test medium 21 (e.g., a type of commercial simulation fluid) is filled into the container 15. The container 15 may be placed onto a lifting platform 22 and within the frame 10a. Alternatively, the frame 10a itself may be closed, such that the test medium (simulation fluid) can be directly filled into the frame, or a simulation organ can be placed directly into the frame such that there is no need to provide a container 15.

Figure 5:
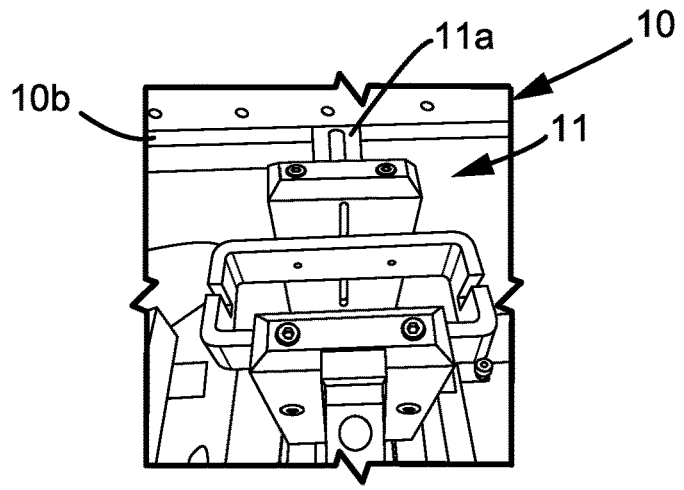
FIG. 5 is a top perspective view of a probe holder of an echogenicity quantitative test system according to the present disclosure.

The ultrasonic probe 16 is fixed into the probe clamp 12, as shown in FIG. 2. The probe clamp 12, together with the ultrasonic probe 16, is placed onto the first guide rod 11a of the probe holder 11, see FIG. 1 (FIG. 5 shows a probe holder 11 with the probe clamp 12 and the ultrasonic probe 16 removed). As mentioned above, the shape of the probe clamp 12 and the probe holder 11 may be modified according to the profiles of ultrasonic probes that are used in particular tests.

The container 15 is moved by the lifting platform 22 to ensure that the ultrasonic probe 16 and the medical device sample 17 are put under the liquid level of the test medium 21 inside the container 15. As such, if the quantitative test for echogenicity is performed on the test medium 21, then the ROI of the test medium can be ensured to be directly below the acoustic path of the ultrasonic probe 16 (i.e., the center of the long axis of the probe).

Further, as shown in FIG. 2, the ultrasonic probe 16 is flat and has a main plane and a thickness. An ultrasonic array acoustic wave emission direction of the probe 16 is parallel to the main plane and perpendicular to the thickness. The main plane of the probe 16 is perpendicular to the liquid level of the test medium 21, and perpendicular to the first guide rod 11a and the second guide rod 13a. As such, as mentioned above, the translating direction of the probe clamp 12 on the first guide rod 11a and the translating direction of the sample clamp 14 on the second guide rod 13a are both perpendicular to the direction of the ultrasound array acoustic wave emission of the probe 16.

Figure 6:
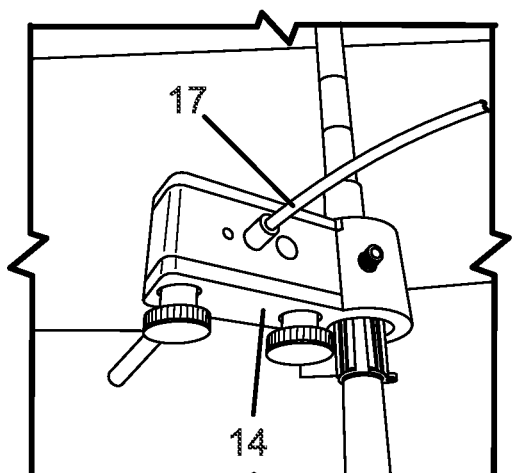
FIG. 6 is a top perspective view of a medical device sample holder of an echogenicity quantitative test system according to the present disclosure.

The medical device sample 17 is clamped into the sample clamp 14 (see FIG. 3, FIG. 6). As mentioned above, the design of the sample clamp 14 can be adjusted according to the profile of the medical device sample (e.g., a balloon catheter).

Moving the probe clamp 12 on the first guide rod 11a or moving the sample clamp 14 on the second guide rod may obtain a suitable distance therebetween, for example, about 10 cm. The distance may vary depending on the type of the medical device to be tested. Further, if the quantitative test for echogenicity is performed on a medical device sample, moving the probe clamp 12 on the first guide rod or moving the medical device sample clamp 14 on the second guide rod 13a can ensure that the medical device sample (and its ROI) is located in the same plane as the ultrasound array emitted by the probe 16.

Figure 7:
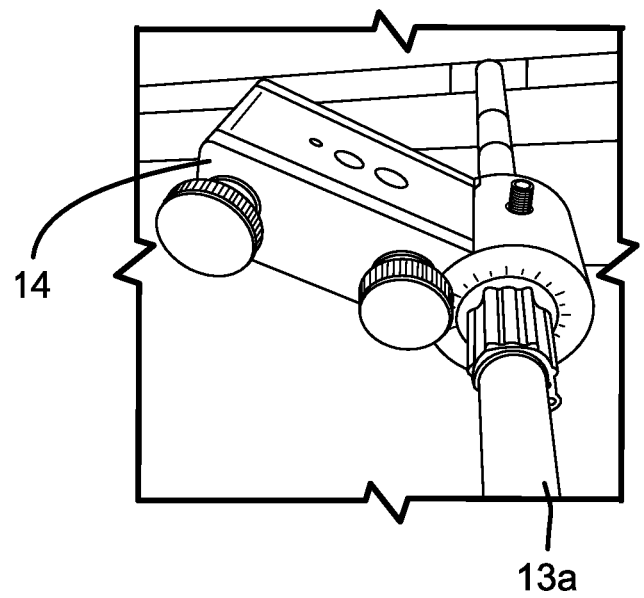
FIG. 7 is an enlarged perspective view of a medical device sample holder of an echogenicity quantitative test system according to the present disclosure, with the medical device sample removed.

Further, as previously mentioned, by rotating the sample clamp 14 in the direction D2 perpendicular to the direction D1 (as shown in FIG. 3), it can be adjusted to a determined angle, for example about 30°, see FIG. 3, FIG. 6 and FIG. 7. The angle could be any for different kinds of medical devices according to their intended uses.

Setting of Ultrasound Diagnostic Device

Firstly, the ultrasound diagnostic device 20 (e.g., a computer programmed to interpret and display signals from the ultrasonic probe 16) is connected to the power. Then, the ultrasonic probe 16 is connected to the device 20, such as by inserting a probe signal line into a socket of the ultrasound diagnostic device. Next, the ultrasound diagnostic device 20 is turned on, such as by way of a switch on a panel of the ultrasound diagnostic device.

According to the present disclosure, if a medical device (balloon dilator) for PCNL surgery is tested, the ultrasound probe 16 and the ultrasound diagnostic device 20 are set to a urinary mode (kidney and ureter). However, other modes may be set according to the intended use of the medical device, such as an abdomen medical device mode, an obstetrics and gynecology medical device mode, a cardiac medical device mode, and so on. Similarly, specific parameters can also be set to other parameters depending on the intended use of the medical device.

Next, images of the sample medical device are captured.

i) The medical device sample 17 is put into the sample holder 13. For example, if a medical device (balloon dilator with an echogenic balloon) for the PCNL surgery is tested, the pre-inflated/inflated balloon is put onto the sample holder 13 with a distal tip depth of 8 cm into the test medium 21. The depth can be varied depending on the intended use of the medical device.

ii) The medical device sample information is recorded in the ultrasonic diagnostic device 20.

iii) The position in a horizontal direction of the sample holder 13 is fine-tuned, such as to make sure that the balloon tip, cone area and part of balloon body show brightest phantom in grayscale image.

iv) At least 3 images for the medical device sample 17 are captured.

v) The medical device sample 17 is taken out of the sample holder 13 and cleaned.

Pixel Analysis (Image Analysis)

Quantitative analysis of grayscale images can be performed with an analysis unit which may be a commercial image processing software, e.g. Adobe Photoshop. The grayscale value for each pixel in the ROI can be read out, and the mean value of grayscale data and the pixel numbers are delivered. The grayscale median can also be delivered, but this is not used in the present disclosure. A region adjacent the ROI with similar pixel numbers should also be analyzed so as to calculate the difference in brightness (i.e. the difference in grayscale) of the ROI from the adjacent region.

Since the clinical improvement of echogenicity should be judged visually by surgeons during operation, the echogenicity improvement should bring a significant difference for the ROI from environment that can be distinguished with naked eyes. Further, the absolute grayscale value for the ROI would bring less clinical benefit than a normalized value, as compared to environment (or an adjacent region) because the absolute data could be affected by many factors. As a result, the relative grayscale value for the ROI to environment can be used as a critical parameter to judge echogenicity.

One step in the pixel analysis is to manually select the ROI from the entire image by recognizing the ROI edges with naked eyes. This subjective action actually requires the same as the surgeon does during the operation, that is, quick monitoring the position of the medical device and making adjustment accordingly. In this process, the surgeon makes a quick decision on the basis of the visual observation of the brightness (i.e. grayscale) of the medical device. Specifically, according to the present disclosure, if pixel analysis is used for calculation, the mean value is used instead of the median.

Pixel analysis may include, but is not limited to, the following specific steps:
1) Providing the ultrasonic diagnostic device with an analysis unit, and opening one image with the analysis unit (such as Adobe Photoshop CS5).
2) Changing the signal channel to brightness.
3) Selecting the ROI with a quick selection tool.
4) Reading the mean value of grayscale and recording it as GS1.
5) Selecting a region adjacent the ROI with a quick selection tool and ensuring that the selected pixel number is consistent with the pixel number that was selected in the step 3).
6) Reading the mean value of grayscale and recording it as GS2.
7) The relative grayscale value for the ROI relative to the adjacent region is defined as RGV=GS1−GS2.
8) At least three images may need to be analyzed for a single medical device sample, repeating step 1) to step 7).
9) The mean value of the at least three RGVs obtained in step 8) will be calculated as a final result.

As used herein, the following terms have the following meanings:

"A", "an", and "the" as used herein refers to both singular and plural referents unless the context clearly dictates otherwise. By way of example, "a compartment" refers to one or more than one compartment.

"About," "substantially," or "approximately," as used herein referring to a measurable value, such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains", and are inclusive or open-ended terms that specifies the presence of what follows e.g. component and do not exclude or preclude the presence of additional, non-recited components, features, element, members, steps, known in the art or disclosed therein.

Although the invention has been described in conjunction with specific embodiments, many alternatives, modifications, and variations will be apparent to those skilled in the art. Accordingly, it embraces all such alternatives, modifications, and variations that fall within the appended claims' spirit and scope. All publications, patents and patent applications mentioned in this specification are herein incorporated in their entirety by reference into the specification, to the same extent as if each individual publication, patent or patent application was specifically and individually indicated to be incorporated herein by reference. In addition, or identification of any reference in this application shall not be construed as an admission that such reference is available as prior art to the present disclosure.

The invention claimed is:

1. An echogenicity quantitative test system for a sample echogenic medical device, comprising:
a test fixture including an ultrasonic probe, a probe holder having a first guide rod, a probe clamp configured to hold the ultrasonic probe and movably held on the first guide rod; and
a holder having a second guide rod and a sample clamp configured to hold the sample echogenic medical device, the sample clamp being movably held on the second guide rod, the first guide rod and the second guide rod being movably disposed relative to the test fixture;
wherein the probe clamp is movable along the first guide rod, while the sample clamp is movable along the second guide rod.

2. The system according to claim 1, wherein the test fixture includes a frame comprising guide rails for receiving the ends of the first and second guide rods.

3. The system according to claim 1, wherein the sample clamp is rotatable about the second guide rod so as to allow an angle adjustment.

4. The system according to claim 1, wherein the test fixture comprises an open frame, and further including a container configured to hold a test medium in which the sample echogenic medical device is located during the test.

5. The system according to claim 4, wherein the container is located on a lifting platform located directly below the ultrasonic probe.

6. The system according to claim 1, wherein the test fixture comprises a closed frame for receiving a test medium.

7. The system according to claim 1, wherein the ultrasonic probe has a main plane and a thickness, wherein an ultrasonic array acoustic wave emitting plane of the ultrasonic probe is parallel to the main plane and perpendicular to the thickness, and the main plane of the ultrasonic probe is perpendicular to the first guide rod and the second guide rod.

8. The system according to claim 1, further including an ultrasonic diagnostic device configured to read a mean grayscale value of a region of interest of the sample echogenic medical device or a test medium, read a mean grayscale value of an adjacent region having a similar number of pixels as a region of interest, and calculate a difference between the mean grayscale value of the region of interest and the mean grayscale value of the adjacent region.

9. The system according to claim 8, wherein the ultrasonic diagnostic device is configured to calculate at least three differences between the mean grayscale value of the region of interest and the mean grayscale value of the adjacent region, and calculate a mean value of the at least three differences.

10. An echogenicity quantitative test system for a sample echogenic medical device, comprising:
a test fixture including an ultrasonic probe, a probe holder having a first guide rod, a probe clamp configured to hold the ultrasonic probe and movably held on the first guide rod; and
a holder having a second guide rod and a sample clamp configured to hold the sample echogenic medical device, the sample clamp being movably held on the second guide rod, the first guide rod and the second guide rod being movably disposed relative to the test fixture;
wherein the test fixture comprises an open frame, and further including a container configured to hold a test medium in which the sample echogenic medical device is located during the test.

11. An echogenicity quantitative test system for a sample echogenic medical device, comprising:
a test fixture including an ultrasonic probe, a probe holder having a first guide rod, a probe clamp configured to hold the ultrasonic probe and movably held on the first guide rod; and
a holder having a second guide rod and a sample clamp configured to hold the sample echogenic medical device, the sample clamp being movably held on the second guide rod, the first guide rod and the second guide rod being movably disposed relative to the test fixture;
wherein the sample clamp is rotatable about the second guide rod so as to allow an angle adjustment.

12. An echogenicity quantitative test system for a sample echogenic medical device, comprising:
a test fixture including an ultrasonic probe, a probe holder having a first guide rod, a probe clamp configured to hold the ultrasonic probe and movably held on the first guide rod; and
a holder having a second guide rod and a sample clamp configured to hold the sample echogenic medical device, the sample clamp being movably held on the second guide rod, the first guide rod and the second guide rod being movably disposed relative to the test fixture;
wherein the test fixture comprises an open frame, and further including a container configured to hold a test medium in which the sample echogenic medical device is located during the test.

13. An echogenicity quantitative test system for a sample echogenic medical device, comprising:
a test fixture including an ultrasonic probe, a probe holder having a first guide rod, a probe clamp configured to hold the ultrasonic probe and movably held on the first guide rod; and
a holder having a second guide rod and a sample clamp configured to hold the sample echogenic medical device, the sample clamp being movably held on the second guide rod, the first guide rod and the second guide rod being movably disposed relative to the test fixture;
wherein the test fixture comprises a closed frame for receiving a test medium.

14. An echogenicity quantitative test system for a sample echogenic medical device, comprising:
a test fixture including an ultrasonic probe, a probe holder having a first guide rod, a probe clamp configured to hold the ultrasonic probe and movably held on the first guide rod; and
a holder having a second guide rod and a sample clamp configured to hold the sample echogenic medical device, the sample clamp being movably held on the second guide rod, the first guide rod and the second guide rod being movably disposed relative to the test fixture;
wherein the ultrasonic probe has a main plane and a thickness, wherein an ultrasonic array acoustic wave emitting plane of the ultrasonic probe is parallel to the main plane and perpendicular to the thickness, and the main plane of the ultrasonic probe is perpendicular to the first guide rod and the second guide rod.

15. An echogenicity quantitative test system for a sample echogenic medical device, comprising:
a test fixture including an ultrasonic probe, a probe holder having a first guide rod, a probe clamp configured to hold the ultrasonic probe and movably held on the first guide rod; and
a holder having a second guide rod and a sample clamp configured to hold the sample echogenic medical device, the sample clamp being movably held on the second guide rod, the first guide rod and the second guide rod being movably disposed relative to the test fixture;
further including an ultrasonic diagnostic device configured to read a mean grayscale value of a region of interest of the sample echogenic medical device or a test medium, read a mean grayscale value of an adjacent region having a similar number of pixels as a region of interest, and calculate a difference between the mean grayscale value of the region of interest and the mean grayscale value of the adjacent region.

* * * * *